United States Patent [19]
Morrison et al.

[11] Patent Number: 5,807,715
[45] Date of Patent: Sep. 15, 1998

[54] METHODS AND TRANSFORMED MAMMALIAN LYMPHOCYTE CELLS FOR PRODUCING FUNCTIONAL ANTIGEN-BINDING PROTEIN INCLUDING CHIMERIC IMMUNOGLOBULIN

[75] Inventors: Sherie L. Morrison, Scarsdale, N.Y.; Leonard A. Herzenberg, Stanford; Vernon T. Oi, Menlo Park, both of Calif.

[73] Assignee: The Board of Trustees of The Leland Stanford Junior University, Stanford, Calif.

[21] Appl. No.: 266,154

[22] Filed: Jun. 27, 1994

Related U.S. Application Data

[63] Continuation of Ser. No. 893,610, Jun. 3, 1992, abandoned, which is a continuation of Ser. No. 675,106, Mar. 25, 1991, abandoned, which is a continuation of Ser. No. 441,189, Nov. 22, 1989, abandoned, which is a continuation of Ser. No. 90,669, Aug. 28, 1987, abandoned, which is a continuation-in-part of Ser. No. 644,473, Aug. 27, 1984, abandoned.

[51] Int. Cl.$^6$ .................... C12N 15/00; C12N 15/13; C07K 16/00
[52] U.S. Cl. ............... 435/69.6; 435/172.3; 435/326; 530/387.1; 530/387.3; 536/23.53
[58] Field of Search ................ 435/69.6, 246.27, 435/320.1, 172.3, 326; 530/387.3, 387.1; 935/15; 536/23.53

[56] References Cited

U.S. PATENT DOCUMENTS

| | | | |
|---|---|---|---|
| 4,399,216 | 8/1983 | Axel et al. | 435/6 |
| 4,816,397 | 3/1989 | Boss | 435/68 |
| 4,816,567 | 3/1989 | Cabilly | 530/387 |

FOREIGN PATENT DOCUMENTS

| | | |
|---|---|---|
| 0125023 | 11/1984 | European Pat. Off. . |
| 8303971 | 11/1983 | WIPO . |

OTHER PUBLICATIONS

Falkner et al Nature vol. 298:286–288, Jul. 1982.
Gillies et al Nucleic Acid Res vol. 11 No. 22:7981–7997, 1983.
Stafford et al Nature vol. 306:77–79, Nov. 1983.
Rice et al., "Regulated expression of an immunoglobulin k gene introduced into a mouse lymphoid cell line", *Proc. Natl. Acad. Sci. USA*, vol. 79, 7862–65 (1982).
Ochi et al., "Functional immunoglobulin M production after transfection of cloned immunoglobulin heavy and light chain genes into lymphoid cells", Proc. Natl. Acad. Sci. USA, vol. 80, 6351–55 (1983).
Sharon, et al., "Expression of a $V_H C_K$ chimaeric protein in mouse myeloma cells", Nature, vol. 309, 364–367 (1984).
Cabilly S. et al 1984 (Jun.) PNAS, USA 81:3273–3277 Generation of Antibody Activity from Immunoglobulin Polypeptide Chains Produced in *Esherichia coli*.
Gillies S.D. et al 1983 Cell 33: 717–728.
Seno et al 1983 Nucleic Acid Research 11(3);719–726.
Dolby et al 1980 PNAS 77(10) 6027–6031 Oct. 1980.
Stedman's Medical Dictionary 25th edition, p. 902, 1992.

*Primary Examiner*—Lila Feisee
*Assistant Examiner*—Julie E. Reeves
*Attorney, Agent, or Firm*—Fish & Neave; Vicki S. Veenker; Edward F. Mullowney

[57] ABSTRACT

Methods for producing functional immunoglobulin are provided. The methods involve transfecting and expressing exogenous DNA coding for the heavy and light chains of immunoglobulin. In some embodiments, chimeric immunoglobulins are provided having variable regions from one species and constant regions from another species by linking DNA sequences encoding for the variable regions of the light and heavy chains from one species to the constant regions of the light and heavy chains respectively from a different species. Introduction of the resulting genes into mammalian host cells under conditions for expression provides for production of chimeric immunoglobulins having the specificity of the variable region derived from a first species and the physiological functions of the constant region from a different species.

62 Claims, 2 Drawing Sheets

METHODS AND TRANSFORMED MAMMALIAN LYMPHOCYTE CELLS FOR PRODUCING FUNCTIONAL ANTIGEN-BINDING PROTEIN INCLUDING CHIMERIC IMMUNOGLOBULIN

This is a continuation of application Ser. No. 07/893,610, filed Jun. 3, 1992, now abandoned, which is a continuation of application Ser. No. 07/675,106, filed Mar. 25, 1991, now abandoned, which is a continuation of application Ser. No. 07/441,189, filed Nov. 22, 1989, now abandoned, which is a continuation of application Ser. No. 07/090,669, filed Aug. 28, 1987, now abandoned, which is a continuation-in-part of application Ser. No. 06/644,473, filed Aug. 27, 1984 now abandoned.

BACKGROUND OF THE INVENTION

1. Field of the Invention

Naturally occurring receptors, such as immunoglobulins, enzymes, and membrane proteins have seen an extraordinary expansion in commercial applications over the last decade. With the advent of monoclonal antibodies, the usefulness of immunoglobulins has been greatly expanded and in many situations has greatly extended prior uses employing polyclonal antibodies. However, in many applications, the use of monoclonal antibodies is severely restricted where the monoclonal antibodies are to be used in a physiological (in vivo) environment. Since, for the most part, monoclonal antibodies are produced in rodents, e.g., mice, the monoclonal antibodies are immunogenic to other species.

While the constant regions of immunoglobulins are not involved in ligand binding, the constant regions do have a number of specific functions, such as complement binding, immunogenicity, cell receptor binding, and the like. There will, therefore, be situations where it will be desirable to have constant regions which bind to cells or proteins from a particular species having binding regions for a particular ligand.

2. Relevant Literature

Kwan et al., *J. Exp. Mod.* (1981) 153:1366–1370 and Clarke et al., *Nucl. Acids Res.* (1982) 10:7731–7749 describe $V_H$ and $V_\kappa$ exons from the mouse phosphocholine-binding antibody-producing S107 myeloma cell line. Oi et al., *Proc. Natl. Acad. Sci. USA* (1983) 80:825–829, report that the mouse light chain gene is not expressed efficiently in a rat myeloma cell.

SUMMARY OF THE INVENTION

Chimeric multi-subunit receptors are provided, where each of the subunits is an expression product of a fused gene. Each fused gene comprises a DNA sequence from one host species encoding the region involved with ligand binding joined to a DNA sequence from a different source, either the same or a different host species, encoding a "constant" region providing a structural framework and biological properties. Introduction of the fused genes into an appropriate eukaryotic host cell under conditions for expression and processing provides for a functional assembled multi-subunit receptor product.

DESCRIPTION OF THE SPECIFIC EMBODIMENTS

Figure 1A:
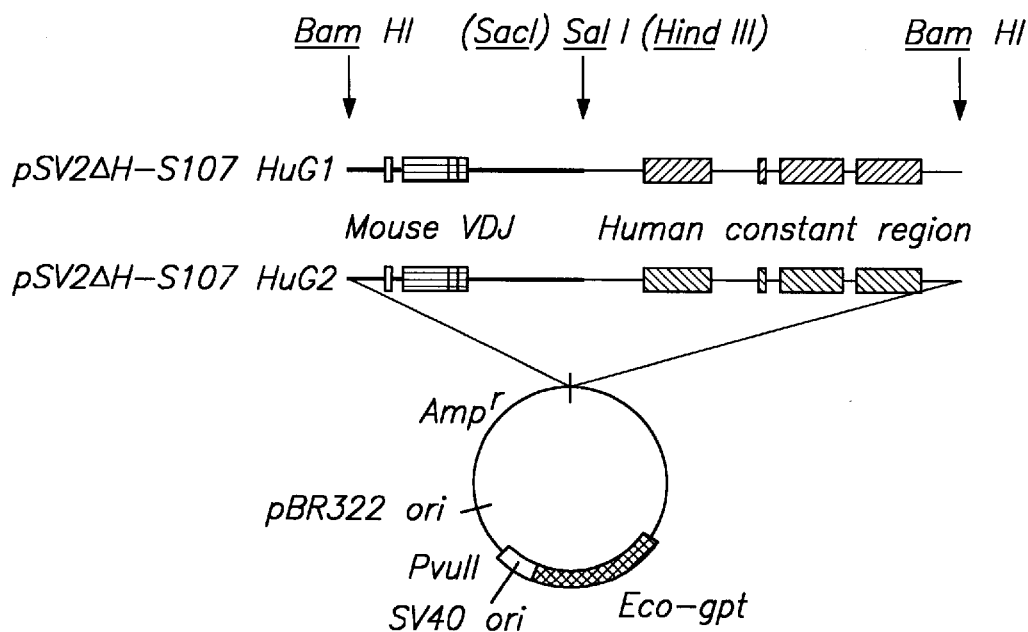
FIG. 1A is a schematic diagram of the chimeric mouse-:human heavy chain gene vector.

Novel methods and compositions are provided, for production of polypeptide products having specific binding affinities for a predetermined ligand and predetermined biological, particularly physiological, properties, each of which are not normally associated with the binding region peptide sequences. Particularly, multi-subunit chimeric receptors are provided which result from fused genes having the portion of the polypeptide involved with binding of a predetermined ligand having an amino acid sequence substantially the same (>90% conserved) as an amino acid sequence having the same function from one host, while the portion involved with providing structural stability, as well as other biological functions, being analogously derived from a different host. The resulting composition can be either an inter- or intraspecies chimera. At least two fused genes are involved, which genes are introduced into an appropriate eukaryotic host under conditions for expression and processing, whereby the fused genes are expressed and the resulting subunits bound together, resulting in an assembled chimeric receptor.

The receptors prepared in accordance with the subject invention will be multi-subunit, where the units are held together either by non-covalent binding or a combination of non-covalent and covalent binding, particularly disulfide linkages through cysteine, and having at least one binding site, usually at least two binding sites, and not more than about ten binding sites. Receptors of interest include both B-cell and T-cell receptors, more particularly, immunoglobulins, such as IgM, IgG, IgA, IgD and IgE, as well as the various subtypes of the individual groups. The light chain may be κ or λ. The heavy chains are referred to as μ, γ, α, δ, and ε.

In discussing the two regions of each subunit, the two regions will be referred to as "variable" and "constant" by analogy to immunoglobulins. The variable region is the region involved with ligand binding and, therefore, will vary in conformation and amino acid sequence depending upon the ligand. The region will usually be composed of a plurality of smaller regions (hypervariable or complementary determining regions), involving a region having as its primary function binding to the ligand (V) and a region associated with joining the V region to the constant region, the joining region (J). There may also be a hypervariable region joining the V and J regions, the diversity region (D). These regions are related to gene segments observed in the genes encoding immunoglobulin variable regions.

The constant region will not be associated with ligand binding and will be relatively limited in the variations in its conformation and amino acid sequence within any one species and within any one class, each class generally having from 1 to 4 subclasses. Each constant region is specific for a species. Within the classes there will be allotypes, individual polymorphisms within a class within a species.

The varible region of the immunoglobulins will be derived from a convenient mammalian source, which may be a rodent, e.g., mouse or rat, rabbit, or other vertebrate, mammalian or otherwise, capable of producing immunoglobulins. The constant region of the immunoglobulin, as well as the J chain for IgM and IgA (not the same as the J region of the heavy or light immunoglobulin chain), will be derived from a vertebrate source different from the source of the variable region, particularly a mammalian source, more particularly primate or domestic animal, e.g., bovine, porcine, equine, canine, feline, or the like, and particularly, humans. The different source of the constant region can be either from a different species or from the same species as the mammalian source utilized to provide the variable region. Thus, the constant region of the receptor will normally be chosen in accordance with the purpose of the receptor. For example, where the receptor is to be introduced into the host, the constant portion will be selected so as to minimize the immune response of the host to the receptor and to optimize biological efficiency, such as complement fixation or physiological half-life (catabolism). Where the receptor is to bind to particular cell membrane surface receptors, the constant region will be chosen in accordance with the host of the receptor recognition site.

The fused gene derived from the two host sources will be prepared by joining the 5'-end of a sequence encoding the constant region in reading frame to the 3'-end of a sequence encoding the variable region. (In referring to 5' or 3' for a double strand, the direction of transcription is with 5' being upstream from 3'.) With immunoglobulins, two fused genes will be prepared, one for the light chain and one for the heavy chain. With T-cell receptors, the two fused genes will be for each of the two chains involved in the formation of the T-cell receptor. The DNA sequences employed for preparation of the fused gene may be derived from a variety of sources. These sources include genomic DNA, cDNA, synthetic DNA, and combinations thereof. The genomic DNA may or may not include naturally occurring introns.

The DNA obtained from natural sources, namely the genomic DNA or CDNA, may be obtained in a variety of ways. Host cells coding for the desired sequence may be isolated, the genomic DNA may be fragmented, conveniently by one or more restriction endonucleases, and the resulting fragments may be cloned and screened with a probe for the presence of the DNA sequence coding for the polypeptide sequence of interest. For the variable region, the rearranged germline heavy chain DNA will include V, D, and J regions, including the leader sequence, which may be subsequently removed as well as any introns. The rearranged germline light chain coding DNA will include the V and J regions including the leader sequence, as well as any introns which may be subsequently removed. The particular source of the exons defining the domains and the manner of splicing, where introns are present, is not germane to this invention. Once the cloned fragment has been identified which contains the desired DNA sequence, this fragment may be further manipulated to remove superfluous DNA, modify one or both termini, remove all or a portion of intervening sequences (introns), or the like.

In providing a fragment encoding the variable region, it will usually be desirable to include all or a portion of the intron downstream from the J region. Where the intron is retained, it will be necessary that there be functional splice acceptor and donor sequences at the intron termini. The gene sequence between the J (joining region) and the constant region of the fused gene may be primarily the intron sequence associated with (1) the constant region, (2) the J region, or (3) portions of each. The last may be a matter of convenience where there is a convenient restriction site in the introns from the two sources. In some instances, all or a portion of the intron may be modified by deletion, nucleotide substitution(s) or insertion, to enhance ease of manipulation, expression, or the like. When the variable region is chosen to be syngeneic with the host cells employed for expression, all or at least about 80% of the intron sequence can be selected from the naturally occurring intron sequence associated with the J region. In some instances it will be necessary to provide adapters to join the intron or truncated intron to the constant region. By cleaving within the intron, the variable region will be separated from its natural constant region.

Alternatively, it may be desirable to have the fused gene free of the intron between the variable and constant regions. Thus, the 3' terminus will be at or in the joining region. Normally all or a portion of the J region will be associated with the host providing the variable region. By restriction enzyme analysis or sequencing of the J region, one can select for a particular site for the 3' terminus of the variable region.

Alternatively, one can use an exonuclease and by employing varying periods of digestion, one can provide for varying 3'-termini, which can then be used for linking to the constant region and selection made for a functional product in a variety of ways. For example, where joining of the variable region to the constant region results in a unique restriction site, the fused DNA fragments may be screened for the presence of the restriction site.

Alternatively, it may be found desirable to include an adapter or linker to join the variable region to the constant region, where the adapter or linker may have the same or substantially the same sequence, usually at least substantially the same sequence, of the DNA sequence of the two fragments adjacent the juncture. The adapter or linker will be selected so as to provide for the two sequences to be in common reading frame. Furthermore, by employing adapters, one could add an additional degree of variability in the binding affinity of the chimeric receptor, by providing for the expression of different amino acids in the J region.

The joining of the various fragments is performed in accordance with conventional techniques, employing blunt-ended or staggered-ended termini for ligation, restriction enzyme digestion to provide for appropriate termini, filling in of cohesive ends as appropriate, alkaline phosphatase treatment to avoid undesirable joining, and ligation with appropriate ligases.

For cDNA, the cDNA may be cloned and the resulting clone screened with an appropriate probe for cDNA coding for the desired variable or constant region. Once the desired clone has been isolated, the CDNA may be manipulated in substantially the same manner as the genomic DNA. However, with cDNA there will be no introns or intervening sequences. The cDNA is cleaved at or near the juncture of the variable region with the constant region so that the variable region is separated from the constant region and the desired region retained. Where a convenient restriction site exists, the CDNA may be digested to provide for a fragment having the appropriate terminus. The restriction site may provide a satisfactory site or be extended with an adapter. Alternatively, primer repair may be employed, where for the variable region a complementary sequence to the site of cleavage and successive nucleotides in the 3' direction of the complementary sequence is hybridized to the sense strand of the CDNA and the nonsense strand replicated beginning with the primer and removal of the single-stranded DNA of the sense strand 3' from the primer. The reverse is true for the constant region. Other techniques may also suggest themselves. Once the fragment has been obtained having the predetermined 3' or 5' terminus, as appropriate, it may then be employed for Joining to the other region.

Finally, one or both of the regions may be synthesized and cloned for use in preparing the fused gene. For the most part, the same or substantially the same constant region can be repetitively used, so that a library of constant regions may be established which can be selected for joining to variable regions. Thus, the constant regions would have an appropriate 5' terminus for joining directly or through an adapter to a variable region.

In order for expression of the fused gene, it will be necessary to have transcriptional and translational signals recognized by an appropriate eukaryotic host. For the most part, desirable eukaryotic hosts will be mammalian cells capable of culture in vitro, particularly leukocytes, more particularly myeloma cells, or other transformed or oncogenic lymphocyte, e.g., EBV transformed cells. Alternatively, non-mammalian cells may be employed, such as fungi, e.g., yeast, filamentous fungi, or the like.

The DNA sequence coding for the variable region may be obtained in association with the promoter region from genomic DNA. To the extent that the host cells recognize the transcriptional regulatory and translational initiation signals associated with the variable region, then the region 5' of the variable region coding sequence may be retained with the variable region coding sequence and employed for transcriptional and translational initiation regulation.

The contiguous non-coding region 5' to the variable region will normally include those sequences involved with initiation of transcription and translation, such as the TATA box, capping sequence, CAAT sequence, and the like. Usually the 5'-non-coding sequence will be at least 150 bp, more usually at least 200 bp, usually not exceeding about 2 kbp, more usually not exceeding about 1 kbp.

The non-coding region 3' to the constant region may be retained for its transcriptional termination regulatory sequences, such as termination and polyadenylation. Thus, by retaining the 3'-region naturally contiguous to the DNA sequence coding for the constant region, the transcriptional termination signals may be provided for the fused gene. Where the transcriptional termination signals are not satisfactorily functional in the expression host cell, then a 3' region functional in the host cell may be substituted. Conveniently, the non-coding 3' region may be obtained from a non-coding contiguous 3' region of a constant region from the expression host. The 3'-non-coding region may be joined to the constant region by any of the means described previously for manipulation and ligation of DNA fragments. This region could then be used as a building block in preparing the fused gene.

The fused gene for the most part may be depicted by the following formula:

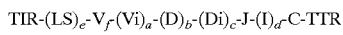

wherein:

TIR intends the transcriptional regulatory and translational initiation region and is generally of at least about 150 bp and not more than about 2 kbp, which may be in whole or in part the sequence naturally joined to the V coding region;

LS refers to a DNA sequence encoding a leader sequence and processing signal functional in the expression host for secretion and processing for removal of the sequence; this leader sequence can contain an intron, as is known in the art to occur;

e is 0 or 1;

V is a segment coding for the variable domain in reading frame with LS, when LS is present;

f is 0 or 1;

D is a segment coding for the diversity domain and is present for the heavy chain (b=1) and is absent for the light chain (b=0);

J is a segment coding for the joining region;

Vi and Di are introns associated with the letter-indicated coding segments having functional donor and acceptor splicing sites;

a, b and c are the same or different and are 0 or 1, wherein when b is 0, c is 0; a, b, and c are all preferably 0;

I is an intron which may be naturally contiguous to the J segment or naturally contiguous to the C domain or a combination of fragments from both, or a fragment thereof, desirably including an enhancer sequence functional in said expression host, or I may be foreign in whole or in part to the J and C segments;

d is 0 or 1 (preferably 0);

C is the constant domain and may code for a $\mu$, $\gamma$, $\delta$, $\alpha$ or $\epsilon$ chain, preferably $\mu$, $\gamma$, or $\alpha$, usually including at least 80% of the constant region sequence, and may be the same as or a modified naturally occurring allotype or an altered constant region encoding an improved protein sequence; and TTR is the transcriptional termination region providing for transcriptional termination and polyadenylation which may be naturally associated with C or may be joined to C, being functional in the expression host; usually being at least about 100 bp and may be 1 kbp or more.

Fused genes lacking, or containing modifications in, the hinge region or other immunoglobulin constant region domains can also be prepared, in like manner to the modifications described above, in which case the formula will be as shown above but with the hinge region of the constant chain being absent or modified.

The constructs for each of the different subunits may be joined together to form a single DNA segment or may be maintained as separate segments, by themselves or in conjunction with vectors.

The subunit constructs may be introduced into a cell by transformation in conjunction with a gene allowing for selection where the construct will become integrated into the host genome.

A large number of vectors are available or can be readily prepared which provide for expression in a host, either by maintenance as an extrachromosomal element or by integration into the host genome. For a mammalian host, a wide variety of vectors are known based on viral replication systems, such as Simian virus, bovine papilloma virus, adenovirus and the like. These vectors can be used as expression vectors where transcriptional and translational initiation and termination signals are present and one or more restriction sites are available for insertion of a structural gene. In addition, the vectors normally have one or more markers which allow for selection of host cells which contain the expression vector. The marker may provide for prototrophy to an auxotrophic host; biocide resistance, e.g., resistance to antibiotics, such as G418, or heavy metals, such as copper; or the like. If desired, expression vectors can be prepared by joining the various components, such as the replication system, markers, and transcriptional and translational regulatory initiation and termination signals in conjunction with the fused gene. Frequently, a vector will include a prokaryotic replication system, which allows for cloning, manipulation, purification, and expansion of the desired DNA sequence.

A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene which has a high level of expression.

Alternatively, promoters from mammalian expression products, such as actin, collagen, myosin, etc., may be employed. Transcriptional initiation regulatory signals may be selected which allow for repression or activation, so that expression of the fused genes can be modulated. Of interest are regulatory signals which are temperature-sensitive so that by varying the temperature, expression can be repressed or initiated, or are subject to chemical regulation, e.g., metabolite.

Once the vector DNA sequence containing the fused gene has been prepared for expression, the DNA construct may be introduced into an appropriate host. Various techniques may be employed, such as protoplast fusion, calcium phosphate-precipitation, or other conventional technique. After the fusion, the cells are grown in a selective medium or are phenotypically selected leaving only cells transformed with the DNA construct. Expression of the fused gene results in assembly to form the receptor. To date, expression has been accomplished in lymphocytes.

The host cells will for the most part be immortalized cells, particularly myeloma or lymphoma cells. These cells may be grown in an appropriate nutrient medium in culture flasks or injected into a syngeneic host, e.g., mouse or rat, or immunodeficient host or host site, e.g., nude mouse or hamster pouch. Particularly, the cells may be introduced into the abdominal cavity for production of ascites fluid and harvesting of the chimeric receptor. Alternatively, the cells may be injected subcutaneously and the antibodies harvested from the blood of the host. The cells may be used in the same manner as hybridoma cells. See Diamond et al., *N. Eng. J. Med.* (1981) 3034:1344 and Kennatt, McKearn and Bechtol (eds.), *Monoclonal Antibodies: Hybridomas—A New Dimension in Biologic Analysis,* Plenum, 1980, which are incorporated herein by reference.

Where a leader is present with a processing signal for secretion and selective cleavage of the leader (signal) sequence, the resulting assembled receptor will be secreted into the nutrient medium of the transformed cells and may be harvested. Where secretion does not occur, after sufficient time for the receptor to be expressed in reasonable amounts, the cells may be killed, lysed, and the receptors isolated and purified. Where transcriptional initiation can be modulated, the cells may be grown to high density under non-permissive conditions, followed by growth under permissive conditions where the receptor is expressed.

The receptors may be naturally glycosylated, unnaturally glycosylated or be free of glycosyl groups, depending on the host, conditions of cellular growth and subsequent treatment. Where a mammalian host cell is employed for expression, usually natural glycosylation will occur. Glycosylation can be prevented by an appropriate inhibitor, e.g., tunicamycin. Alternatively, glycosyl groups may be removed by hydrolysis, e.g., enzymatic hydrolysis using hydrolases. In expression hosts other than mammalian cells, unglycosylated or unnatural glycosylated receptors may be obtained.

The receptor may be isolated and purified in accordance with conventional conditions, such as extraction, precipitation, chromatography, affinity chromatography, electrophoresis, or the like. By employing antibodies specific for the constant region(s), affinity chromatography will allow for concentration and purification of the chimeric receptor.

The chimeric receptors can be used in the same manner as other receptors for binding to specific ligands in diagnostic assays, affinity chromatography or the like. In addition, because a chimeric receptor of substantially reduced immunogenicity can be produced, the chimeric receptors can find use in therapy, for passive immunization for in vivo imaging, for specific treatment of diseased cells, or the like. For in vivo imaging, the chimeric antibody will normally be conjugated to a radionuclide, e.g., technetium, rhenium, or the like. For biocidal activity, the antibody may be joined to the A-portion of toxins, liposomes containing biocidal reagents, radionuclides, or other biocidal agent. Alternatively, the antibodies can be used in combination with the host immune system, e.g., complement, due to the presence of the native constant region. In vitro, the subject chimeric antibodies can be used in conjunction with complement to remove particular cells from a mixture of cells, where the target cells have a ligand complementary to the binding site of the chimeric antibody.

The following examples are offered by way of illustration and not by way of limitation.

EXAMPLE 1

Materials and Methods

Chimeric Genes

Figure 1B:
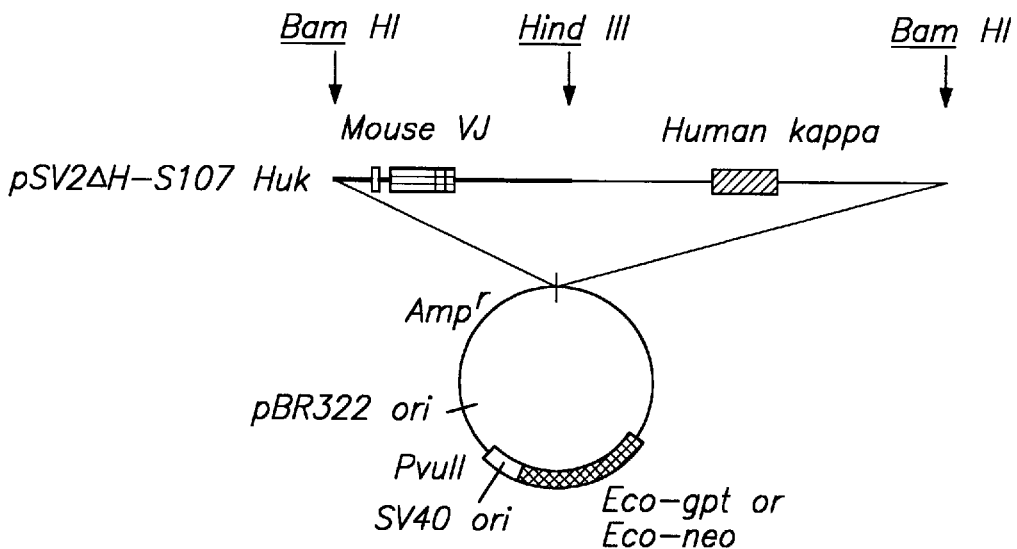
FIG. 1B is the chimeric light chain vector.

The cloned S107 variable region (heavy) (VH) and S107 Vκ variable region (light, kappa) genes were obtained from Dr. Matthew Scharff (Dept. of Cell Biology, Albert Einstein College of Medicine, Bronx, N.Y. 10641). The S107 VH gene was spliced to human IgG1 and IgG2 constant region genes using SalI linkers as shown in FIG. 1A. Both constructs were inserted into the vector pSV2ΔH-gpt (Oi et al., *Proc. Natl. Acad. Sci. USA* (1983) 80:825–829; Mulligan and Berg, *Science* (1980) 209:1422–1427). The S107 Vκ gene was spliced to the human κ gene at a unique HindIII site located in the large intron between the Jκ and Cκ exons as shown in FIG. 1B. This chimeric light chain gene construct was inserted into both pSV2ΔH-gpt and pSV2-neo plasmid vectors (Mulligan and Berg, *Proc. Natl. Acad. Sci. USA* (1981) 78:2072–2076) and pSV184ΔH-neo plasmid vectors (Oi and Morrison, *Biotechniques* (1986) 4:214–221).

Transfection

Protoplast fusion and calcium-phosphate ($CaPO_4$) precipitation techniques (Oi et al., (1983) supra; Sandri-Goldin et al., *Mol. Cell. Biol.* (1981) 1:743–752; Chu and Sharp, *Gene* (1980) 13:197–202) were used to transfect these chimeric immunoglobulin genes into the J558L myeloma cell line (a lambda (λ) light chain producing mouse myeloma cell line) and the non-immunoglobulin-producing An derivative of the P3 myeloma cell line. Mycophenolic acid (Gibco Laboratories, Santa Clara, Calif. 95050) was used for selection of cells transfected with pSV2ΔH-gpt vectors as described previously (Oi et al., (1983) supra; Ochi et al., *Proc. Natl. Acad. Sci. USA* (1983) 80:6351–6355). G418 (Gibco Laboratories) at 1.0 mg/ml was used for selection of cells transfected with pSV2-neo vectors (Mulligan and Berg, (1980) supra).

When both light and heavy chimeric genes were transfected into the J558L cell line using protoplast fusion techniques, light and heavy chimeric immunoglobulin genes were transfected sequentially using G418 selection for the chimeric light chain gene vector and mycophenolic acid for the chimeric heavy chain gene vector. The protoplast fusion transfection procedure used was as described previously (Oi et al., (1983) supra).

Transfection using the calcium phosphate precipitation procedure was done by mixing 40 µg of both chimeric light and chimeric heavy chain pSV2ΔH-gpt vectors and transfecting a total of 80 µg of plasmid DNA into $5 \times 10^6$ cells. Mycophenolic acid was used to select for transformed cell lines as described previously (Oi et al., (1983) supra).

Antigen-binding

Phosphocholine (PC) binding of antibody secreted into the culture supernates of transfected cell lines was analyzed using a solid-phase radioimmunoassay described previously (Oi and Herzenberg, *Mol. Immunol.* (1979) 16:1005–1017). PC-binding antibodies in biosynthetically-labeled culture supernates and cell lysates of transfected cell lines also were analyzed by binding the biosynthetically-labeled antibody to PC-coupled to Sepharose 4B (Pharmacia Five Chamicals, Piscataway, N.J.) and then eluting the bound antibody with PC-hapten. The bound and eluted antibody was examined by SDS-polyacrylamide gel electrophoresis (SDS-PAGE). Biosynthetic-labeling procedures were done as described previously (Oi et al., *J. Exp. Med.* (1980) 151:1260–1274).

Idiotype Analysis

Three hybridoma anti-idiotope antibodies, obtained from Dr. Matthew Scharff (Dept. of Cell Biology, Albert Einstein College of Medicine, Bronx, N.Y.), were used to analyze the variable heavy-variable light (VH-VL) domain structure of the chimeric human anti-PC antibodies. These antibodies, recognizing three independent idiotopes, were used to immunoprecipitate biosynthetically-labeled material eluted with PC from the PC-Sepharose 4B matrix. Immunoprecipitates were analyzed by SDS-PAGE.

Immunoglobulin Chain Composition

Monoclonal anti-human IgG and anti-human κ antibodies (Becton-Dickinson Monoclonal Center, Mt. View, Calif.) were used to immunoprecipitate biosynthetically-labeled chimeric human anti-PC antibodies for analyses using two-dimensional non-equilibrium pH gradient polyacrylamide gel electrophoresis (NEPHGE) (Oi and Herzenberg, (1979) supra). PC-coupled to Sepharose 4B also was used for immunoprecipitations.

Immunoglobulin Heavy Chain Glycosylation

Tunicamycin (Calbiochem-Behring, San Diego, Calif.) was used to inhibit asparagine-linked glycosylation of biosynthetically-labeled antibody from mouse cell lines producing mouse:human chimeric immunoglobulins (Oi et al., (1980) supra). PC-binding antibody from tunicamycin-treated cells was analyzed by SDS-PAGE. Procedures used for tunicamycin treatment were as described previously (Oi et al., (1980) supra).

Chimeric Mouse:Human Antibody Production in Mice

Transformed J558L cells producing chimeric mouse:human antibody were injected subcutaneously into BALB/c mice ($10^6$ cells/mouse). Sera from tumor-bearing mice were analyzed for human anti-PC antibody by a solid-phase radioimmunoassay described previously (Oi and Herzenberg, (1979) supra) and by immunoelectrophoresis using a polyclonal anti-human antiserum.

Results

Expression of chimeric mouse V:human C region genes in transfected mouse myeloma cells J558L and the non-immunoglobulin-producing P3 myeloma cell lines was obtained. When both light chain and heavy chain chimeric genes were transfected into the same cell, tetrameric (H2L2) antigen-binding antibodies were obtained. Autoradiograms of two-dimensional NEPHGE analyses of the chain composition of biosynthesized and secreted antibody molecules bound and eluted from phosphocholine-Sepharose showed the formation of mixed molecules, including the endogenously produced J558L λ light chain. Each polypeptide chain had the expected charge and relative molecular weight. Identical two-dimensional gel analyses results were obtained with immunoprecipitates with monoclonal anti-human K and IgG antiodies. Similar results were obtained from immunoprecipitates of human $IgG_2(\kappa)$ antibodies produced by transfected P3 cell lines. Since the non-immunoglobulin-producing parental P3 cell line does not produce endogenous immunoglobulin polypeptide chains, as expected only the chimeric mouse:human heavy and light chains are seen on the autoradiograms.

Phosphocholine-binding by the chimeric antibody produced in the J558L cell line was the result from specific association of the chimeric immunoglobulin light and heavy polypeptide chains, i.e., the VH and Vκ domains of the S107 myeloma protein connected to human constant region polypeptides. This was determined by measuring PC-binding by immunoglobulins produced by J558L cells transfected with the mouse: human chimeric heavy chain gene. PC-binding was never observed from antibody secreted by transfected J558L cells expressing only the chimeric heavy chain and the endogenous J558L λ light chain (data not shown). Chimeric antibodies produced in the transfected non-immunoglobulin-producing P3 cell line also were shown to bind PC-Sepharose. In view of the low binding affinity of the parental mouse S107 antibody, analyses of appropriate polypeptide folding of mouse VH and Vκ domains in the novel environment of human constant regions polypeptide chains were done by determining the presence of idiotypes known to occur on the parental S107 PC-binding antibody molecule. Three monoclonal anti-idiotope antibodies, each recognizing a distinct epitope on the light and heavy variable region domains and an epitope defined by the presence of both light and heavy variable region domains, were found to react with the mouse:human chimeric anti-PC antibodies. This strongly supports the fact that the mouse S107 antigen-binding domains have folded into their intended structures.

Glycosylation of the mouse:human chimeric antibodies in mouse myeloma cells was analyzed by measuring the relative molecular weight (Mr) of antibodies biosynthesized in the presence and absence of tunicamycin, a known antibiotic inhibitor of asparagine-linked glycosylation. Autoradiograms of SDS-PAGE analysis of the chimeric heavy and light chains produced in mouse myeloma cells in the presence or absence of tunicamycin showed the lower relative Mr of the heavy chain synthesized in the presence of tunicamycin as expected if a single N-linked carbohydrate was absent from the polypeptide chain. From these data it is concluded that the mouse myeloma cell appropriately glycosylates the human heavy chain.

When transfected J558L cells producing the human IgG2 (κ) chimeric anti-PC antibody were grown as a subcutaneous tumor in BALB/c mice, analysis of the sera of these mice showed significant human IgG2(κ) anti-PC binding antibody production by radioimmunoassay. Polyclonal anti-human antiserum demonstrated the presence of significant quantities of human immunoglobulin in the sera. Based on comparison with prior experience with mouse hybri-doma-antibody production in mice, the amount of immunoglobulin visualized by immunoelectrophoresis analysis of mice bearing tumors of the transfected J558L cell line was similar to the lower levels of production seen with other mouse hybridoma tumor cell lines.

Analysis showed that fewer than about 10% of the transfected cell lines produced both chimeric heavy and light chain polypeptides. Among transformants generated by protoplast fusion, both gpt and neo biochemical markers were expressed at expected frequencies. However, chimeric light chain expression was infrequent. In co-transfection experiments using the $CaPO_4$ precipitation protocol, the same phenomenon was observed.

Based on prior experience with co-expression of gene products in transformed cell lines, it appears that the appropriate transcriptional or translational controlling elements are absent in either the chimeric light chain gene construct or in the mouse myeloma cell lines used. The mouse Vκ gene promoter is coupled to the presumed human intronic DNA sequences that are homologous to the known mouse intronic controlling element (ICE) or immunoglobulin "enhancer" element (Morrison and Oi, *Ann. Rev. Immunol.* (1984) 7:239–256). The chimeric mouse: human heavy chain gene is not constructed in this manner and, in contrast, is expressed efficiently. The mouse heavy chain intronic controlling element (ICE) sequences are included and human sequences excluded in this construct. The basis for the low level of expression of the light chain is subject to speculation.

It is evident from the above results that chimeric receptors, as illustrated by immunoglobulins, can be produced where the variable regions may be obtained from one host source and the constant regions obtained from another host source. Where the immunoglobulins are to be use in vivo, this can provide for numerous advantages, such as reduced immunogenicity, a lower catabolism, and the ability to fulfill biological effector functions associated with the constant regions. Furthermore, now that it is shown that chimeric receptors can be produced, there is the opportunity to prepare chimeric receptors with modification of V, J, and D regions so as to modify binding specificity.

EXAMPLE 2

Figure 2:
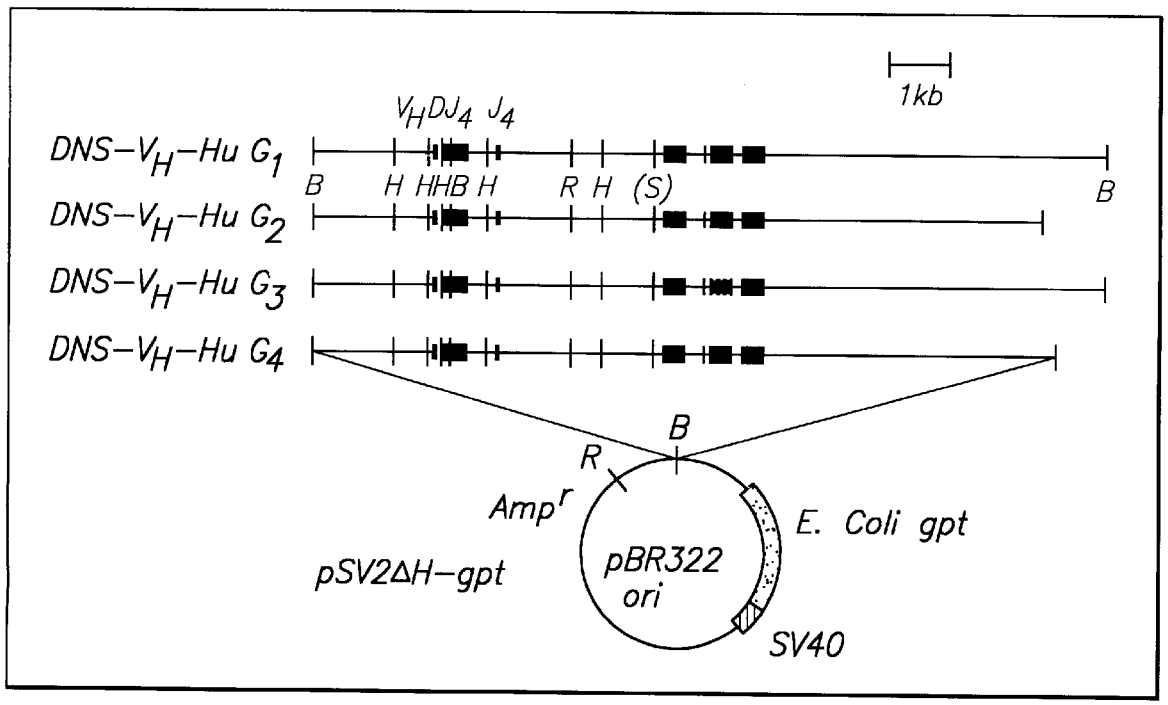
FIG. 2 is a schematic diagram of chimeric human IgG anti-DNS expression vectors.

A family of recombinant anti-DNS antibodies was prepared by cloning the mouse $V_H$ gene expressed in the DNS1 (27–44) hybridoma cell line (Dangl et al., *Cytometry* (1982) 2:395) and joining this gene to the already cloned human $IgG_1$, $IgG_2$, $IgG_3$, $IgG_4$, rabbit IgG and mouse $IgG_3$ heavy chain constant region genes. These recombinant genes were inserted into the eukaryotic expression vector, pSV2(delta) H-gpt (Oi et al., *BioTechniques* (1987) 4:214). Each recombinant vector was transfected into a heavy chain loss mutant of the DNS1 hybridoma cell line, 27–44.A5C13, or co-transfected with a DNS-$V_K$ expression vector into the Ig⁻ cell line SP2.0 to generate stable anti-DNS transfectoma cell lines (Morrison and Oi, *Ann Rev. Immunol.* (1984) 2:239). The expressed $V_H$ and $V_K$ genes from the DNS1 hybridoma (Oi et al., *Nature* (1984) 307:136; Reidler et al., *J. Mol. Biol.* (1982) 158:739) were cloned from phage lambda libraries (Dangl, thesis, Stanford University, Stanford, Calif.) and used to construct the vectors shown in FIG. 2. Transfection by protoplast fusion and selection and screening of transfectomas has been described (Oi et al., *BioTechniques,* supra; Dangl, thesis, Stanford University, Stanford, Calif.). Anti-DNS antibodies were purified from culture supernate by affinity chromatography using a dansyl isomer 2-dimethylaminonaphthyl-5-sulfonamide-3-lysine as absorbant (coupled to AH-Sepharose-4B) and eluant. The affinity of the DNS1 combining site for DNS is 17 nM; the binding affinity of this isomer is lower by a factor of $10^3$, making it suitable for use in affinity purification. Removal of bound hapten by dialysis was monitored by fluorescence emission spectroscopy. Antibodies were pure, >95% and free of aggregates as determined by size exclusion chromatography (Dangl, thesis, Stanford University, Stanford, Calif.). The chimeric mouse-human immunoglobulin heavy chain vectors are depicted in FIG. 2. The rabbit IgG and mouse $IgG_3$ heavy chain vectors were similarly constructed.

The nature of the DNS combining site of the genetically engineered antibodies was monitored by measuring the fluorescence emission spectra of bound DNS-lysine. This hapten is a sensitive indicator of the dynamic polarity of its microenvironment. Independently derived mouse $IgG_1$ anti-DNS antibodies with different combining sites were previously shown to generate different emission spectra (Reidler et al., *J. Mol. Biol.* (1982) 158:739). The absorption and emission spectra of DNS-lysine bound to each genetically engineered antibody was identical to the DNS1 combining site of the parental hybridoma (corrected fluorescence emission spectra of each affinity purified chimeric antibody were measured using a SIM model 8000 fluorescence spectrophotometer with 340 nm excitation, essentially as described in Reidler, et al., *J. Mol. Biol.* (1982) 158:739). This indicates that each chimeric antibody has a properly folded $V_H$ domain, despite the heterologous junction between the mouse $V_H$ and human or rabbit $C_{H1}$ domains. Stable transfectoma cell lines produced immunoglobulins with heavy chains of appropriate size and charge as determined by two-dimensional sodium dodecyl-sulfate polyacrylamide gel electrophoresis (SDS-PAGE). Immunoglobulins produced by each transfectoma cell line were analyzed by biosynthetic labelling, immunoprecipitation and one- or two-dimensional SDS-PAGE essentially as described by P. P. Jones in *Selected Methods in Cellular Immunology,* B. B. Mishell, S. M. Shiigi, Eds. (W. H. Freeman, San Francisco, 1980), pp. 238. Rabbit anti-human IgG anti-sera was purchased from Cappel. The recombinant heavy chains are glycosylated, a post-translation modification known to affect biosynthetic labeling in the presence or absence of tunicamycin, an antibiotic known to inhibit asparagine-linked glycosylation (Hickman and Kornfeld *J. Immunol* (1978) 121:990; Nose and Wigzell *Proc, Natl. Acad. Sci.* (1983) 80:6632; Leatherbarrow et al. *Molec. Immunol.* (1985) 22:407).

This Example demonstrates the ability to prepare interspecies chimeric antibodies from additional species using the previously described techniques as well as the ability to produce intra-species chimerics.

EXAMPLE 3

A series of intra-species hybrid mouse $IgG_1$-$IgG_{2a}$ immunoglobulins all with identical light chains and variable regions were produced. Hybrid heavy chain constant region gene segments were generated by genetic recombination in *E. coli* between plasmids carrying mouse γ1 and γ2a gene segments. Crossovers occurred throughout these segments although the frequency was highest in regions of high nucleotide sequence homology. Eleven hybrid proteins were produced by transfection of a variant hybridoma cell line. Immunoglobulins produced by the transfected cell lines were assembled into $H_2L_2$ tetramers and properly glycosylated in addition to having identical antigen combining sites specific for the fluorescent hapten ε-dansyl-L-lysine. Protein A binding, used as a probe of Fc structure in these variant antibodies was consistent with the identity of protein A contact residues within the Fc. Novel receptors with new and improved functions were created, demonstrating that improvements over naturally occurring receptors can be made.

Materials and Methods

Generation of hybrid genes

Hybrid $C_H$ gene segments coding for polypeptides with an $IgG_1$ amino-terminus and an $IgG_2$a carboxy-terminus or an $IgG_{2a}$ amino-terminus and $IgG_1$ carboxy-terminus were generated by adaptation of the system described by Schneider et al., *Proc. Natl. Acad. Sci.* (1981)

78:2169–2173. Plasmid pHGX1 was constructed by digesting pBN2 (Nichols and Yanofsky, *Proc. Natl. Acad. Sci.* (1979) 76:5244–5248) with HindIII and PvuII, filling in the overhanging HindIII ends with $T_4$ DNA polymerase, ligating XbaI linkers to the flush ends, and recircularizing the plasmid. Plasmids pHGX1$C_{\gamma 2a}$A and pHGX1$C_{\gamma 2a}$B were generated by digesting pγ2a.9 with EcoRI and HindIII, filling in the overhanging ends, ligating XbaI linkers to the blunt ends, and inserting the $C_{\gamma 2a}$-containing fragment into XbaI-digested pHGX1. Plasmids pHGX1$C_{\gamma 2a}$A and pHGX1$C_{\gamma 2a}$B differ only in the orientation of the inserted fragment. Plasmid pHGX2 was constructed by digesting pWS1 (Schneider et al., *Proc. Natl. Acad. Sci.* (1981) 78:2169–2173) with HpaI and SalI, filling in the overhanging SalI end, ligating XbaI linkers to the flush ends, and recircularizing the plasmid. Plasmids pHGX2$C_{\gamma 1}$A and pHGX2$C_{\gamma 1}$B were generated by digesting $P_{\gamma 1}$ with KpnI, and ligating the $C_{\gamma 2a}$-containing fragment to XbaI-digested pHGX2. Plasmids pHGX2$C_{\gamma 1}$A and pHGX2$C_{\gamma 1}$B differ only in the orientation of the inserted fragment.

E. coli strain W3110 trpR ΔtrpEA2 tnaA2 rna-19 was transformed with both pHGX1$C_{\gamma 2a}$A and pHGX1$C_{\gamma 1}$A or pHGX1$C_{\gamma 2a}$B and pHGX1$C_{\gamma 1}$B to chloramohenicol resistance ($Cm^r$) and ampicillin resistance ($Amp^r$). Single colonies were transferred to L broth containing chloramphenicol (20 mg/l) and ampicillin (100 mg/l) and grown overnight. Cells were collected by centrifugation, washed with Vogel-Bonner minimal medium (Vogel and Bonner, *J. Biol. Chem.* (1956) 218:97–106), and plated on minimal plates supplemented with glucose (0.4%), acid-hydrolyzed casein (0.5%), indole (10 mg/l) and chloramphenicol. Individual colonies were transferred to identical liquid medium and grown overnight. Plasmid DNA was extracted from these cultures, and the monomeric double crossover plasmids isolated by size fractionation using agarose gel electrophoresis. DNA from monomeric plasmid fractions was used to transform *E. coli* W3110 trpR ΔtrpEA2 tnaA2 rna-19 to $Trp^+$ and $Cm^r$. Transformants were screened for ampicillin sensitivity ($Amp^s$) by replica plating.

The crossover site generating each hybrid was located by restriction enzyme analysis. Precise crossover junctions were identified by DNA sequencing by the method of Maxam and Gilbert *Methods Enymol.* (1980) 65:499–560 or Sanger and Coulson, *Proc. Natl. Acad. Sci.* (1977) 74:5463–5467 using M13mp9 (Messing and Vieira, *Gene* (1982) 19:269–276) to generate single-stranded DNA template.

An additional variant heavy chain gene, one lacking the hinge region exon, also was constructed. The XbaI ends of fragments containing $C_H$ gene segments were filled in and converted to SalI ends with linkers. These fragments were ligated into the SalI site of pMLSVgpt DNS-$V_H$·A$\gamma_{2a}$ heavy chain constant region with a hinge exon deletion was constructed by removing a StuI-SmaI fragment from an expression vector carrying the $\gamma_{2a}$ $C_H$ coding region. This plasmid is designated pMLSVgpt DNS-$V_H C_{\gamma 2a}$Δ hinge.

Transfection of Hybrid Heavy Chain Genes

Plasmids designed to express anti-DNS hybrid heavy chain genes were constructed as described above. The pMLSVgpt DNA-$V_H$ contains the *E. coli* xanthine-guanine phosphoribosyltransferase gene (gpt) which is used to biochemically-select transfected mammalian cells (Mulligan and Berg, *Proc. Natl. Acad. Sci.* (1981) 78:2072–2076). The heavy chain variable region ($V_H$) gene segment from the anti-DNS hybridoma 27–44 (Dangi et al., *Cytometry* (1982) 2:395–401) is located upstream of the $C_H$ gene insertion site. Hence ligation of each recombinant heavy chain constant region gene segment into pMLSVgpt DNA-$V_H$ in the proper orientation generates a gene encoding the corresponding variant anti-DNS heavy chain polypeptide. Hybrid anti-DNS antibody-producing cell lines were generated by transfecting these recombinant vectors into a heavy-chain-loss variant of the 27–44 hybridoma cell line, designated 27–44 A5C13 (which was provided by Dr. D. Parks of Stanford University). Other hybridoma cell lines lacking production of the heavy chain could also be used.

Expression vectors were transfected into 27–44 A5C13 using the following protoplast fusion procedure. *E. coli* strain HB101 carrying the appropriate plasmid was grown in L broth to an $OD_{600}$ of 0.6–0.7. Plasmid copy number was amplified by addition of chloramphenicol (170 mg/l) and incubating cultures overnight. Cells from 25 ml of culture were harvested by centrifugation and gently resuspended in 1.25 ml of ice cold 20% sucrose, 50 mM Tris-HCl pH 8.0. Freshly prepared lysozyme solution (0.25 ml at 5 mg/ml in 0.25M Tris-HCl pH 8.0) was added and the suspension incubated for 6 minutes on ice. A 0.5 ml aliquot of 0.25 mM EDTA pH 8.0 was added and the mixture was incubated for 5 minutes on ice. Following addition of 0.5 ml of 50 mM Tris-HCl pH 8.0, the cells were incubated for 10 minutes at 37° C. The bateria were then diluted with 10 ml of RPMI 1640 medium supplemented to 10% sucrose and 10 mM $MgCl_2$ and warmed to 37° C. After incubation for 10 minutes at room temperature, the protoplasts were used for fusion.

The 27–44 A5C13 cell line was grown to a density of 0.3 to $1 \times 10^6$ cells/ml in RPMI 1640 medium containing 1.0-mM sodium pyruvate, 2.0 mM L-glutamine, 50 mM β-mercaptoethanol, 10% fetal calf serum (FCS), and 1% NuSerum™ (Collaborative Research, Lexington, Mass.). Cells ($2 \times 10^7$) were harvested by centrifugation and resuspended in 1 ml of RPMI 1640 medium with supplements. After addition of 3 ml of protoplast suspension, the cells were pelleted by centrifugation. The pellet was resuspended by slowly adding 1 ml of 45% polyethylene glycol (PEG) in RPMI 1640 medium without supplements (warmed to 37° C.) while mixing gently for 1 to 2 minutes. Nine milliliters of 37° C. RPMI medium without supplements were added slowly to dilute the PEG solution. The suspension was centrifuged and the pellet resuspended in 12 ml of RPMI 1640 medium. Cells were then dispensed into a 24-well plate in 0.5 ml aliquots. The following day, 1 ml of RPMI 1640 medium was added to each well. Two days after fusion, transfected cell lines were selected in medium containing 1 mg/l mycophenolic acid, 15 mg/l hypoxanthine, and 200 mg/l xanthine. Cultures were fed with 1 ml of selection medium as needed.

Protein Characterization

Antibodies from transfected cell lines were biosynthetically-labelled with [$^{35}$S]-methionine in the absence and presence of tunicamycin. Antibodies were immunoprecipitated with rabbit anti-mouse immunoglobulin antisera and analyzed by SDS-polyacrylamide gel electrophoresis (SDS-PAGE), two-dimensional non-equilibrium pH gradient gel electrophoresis, and two-dimensional non-reducing-reducing polyacrylamide gel electrophoresis (Goding, *Handbook of Experimental Immunology, Vol.* 1. Blackwell Scientific Publications, Oxford (1986) 20:1–20.33). Fluorescence emission spectra of hybrid anti-DNS antibodies bound to ε-dansyl-L-lysine were measured using 340 nm excitation on a SLM model 8000 fluorescence spectrophotometer.

Production and Purification of Genetically Engineered Antibodies

Hybrid anti-DNS antibodies were purified from sera of tumor-bearing mice or from culture supernates of transfected cell lines grown in serum-free medium (Hana Biologicals, Berkeley, Calif.). Hybridoma cell lines 27–44 and 27–13 were used to produce parental IgG$_1$ and IgG$_2$a anti-DNS antibodies (Dangl et al., *Cytometry* (1982) 2:395–401).

Anti-DNS antibodies were purified by affinity chromatography using a DNS analog (2-dimethylaminonaphthyl-5-sulfonyl chloride; Molecular Probes, Eugene, Oreg.) coupled to AH-Sepharose 4B (Pharmacia, Piscataway, N.J.). N-(5-Carboxypentyl)-2-dimethylaminonaphthyl-5-sulfonamide was used to elute bound antibody.

Protein A Binding

Binding of each hybrid anti-DNS antibody to *Staphylococcus aureus* protein A was measured at pH 7.0. Purified protein A (Pharmacia) and a two-fold molar excess of IgG were incubated in 150 mM sodium phosphate pH 7.0 for 20 minutes at room temperature. IgG-protein A complexes were analyzed using Superose 6 column chromatography (Pharmacia).

Results

Generation of Hybrid $C_H$ Genes

Genetic recombination between pHGX1C$_{\gamma 2a}$A and pHGX1C$_{\gamma 1}$A or pHGX1C$_{\gamma 2a}$B and pHGX1C$_{\gamma 2a}$B yielded TRP$^+$ colonies at frequencies similar to that reported previously (Schneider et al., supra). The Trp$^+$ phenotype results from a single crossover between trpB segments in the two parental plasmids to generate an intact, functional gene. The single crossover produces a dimeric plasmid, containing the entire genetic material of both starting plasmids. The dimeric trpB$^+$ Cm$^r$ Amp$^r$ plasmid is expected to sustain a second recombinational event in any region of homology. A second crossover, between C$_\gamma$1 and C$_\gamma$2a gene segments, yields a monomeric trpB$^+$ Cm$^r$ Amp$^s$ plasmid with a hybrid $C_H$ segment. Transformation of *E. coli* W3110 trpR ΔtrpEA2 tnaA2 rna-19 with size-fractionated monomeric plasmid DNA from trpB$^+$ cells, followed by selection for Trp$^+$ and Cm$^r$, yielded only monomeric trpB$^+$ Cm$^r$ Amp$^s$ plasmids that always carried hybrid $C_H$ gene segments.

Seventy independently derived hybrid $C_H$ gene segments were recovered. Ten of the most diverse recombinant immunoglobulin heavy chain constant region gene segments were selected for further study. Six have an IgG$_1$ amino-terminus and an IgG$_{2a}$ carboxy-terminus (designated $\gamma_1\gamma_{2a}^{-2\ through\ -7}$). Five of these six recombinant molecules were generated by crossovers in the $C_H$2 exon; the sixth was generated by a crossover in the intron between the $C_H$1 and hinge exons. Two recombinants (designated $\gamma_{2a}\gamma_1^{-1\ and\ -2}$) are IgG$_{2a}$-IgG$_1$ hybrids; one generated by a crossover in the $C_H$2 exon and the other by a crossover in the intron between the $C_H$1 and hinge exons. Two other recombinants ($\gamma_1\gamma_{2a}^{-1\ and\ -8}$) were included for study as controls. They encode parental $\gamma_1$ and $\gamma_{2a}$ heavy chain polypeptides and arose from crossovers in DNA sequences flanking immunoglobulin coding regions.

Precise crossover points were determined by DNA sequencing. The amino acid sequences of the parental IgG$_1$ and IgG$_{2a}$ polypeptides as well as the deduced sequence junctions of the ten recombinant heavy chains were determined. Nine of the ten hybrid genetic segments appear to have been generated by single crossover events, while $\gamma_1\gamma_{2a}^{-1}$ appears to have arisen by a triple exchange within the intron between $C_H$1 and hinge exons. The length of nucleotide sequence identity between $C_{\gamma 1}$ and $C_{\gamma 2a}$ gene segments within which exchanges occurred varied from 5 to 21 base pairs.

Expression of Recombinant Immunoglobulins Genes

All eleven heavy chain genes are expressed when transfected into the 27–44 A5C13 cell line. SDS-PAGE analyses show that each cell line synthesizes and secretes, in addition to light chain (L), an immunoglobulin heavy chain (H) polypeptide of the appropriate relative molecular weight (Mr). Two-dimensional nonequilibrium pH gradient gel electrophoresis analysis confirmed the identity of the endogenous light chain produced by each transfected cell line, as well as the expected charge (deduced from the amino acid sequence) for each recombinant heavy chain polypeptide. Each recombinant antibody, when synthesized in the presence of tunicamycin showed an altered mobility upon reducing SDS-PAGE relative to each antibody synthesized in the absence of tumicamycin indicating that each heavy chain is glycosylated.

The DNS fluorescence emission spectrum of all eleven recombinant antibodies are identical to the hybridoma IgG$_1$ and IgG$_{2a}$ anti-DNS antibody fluorescence emission spectra. This is an accurate and sensitive means of identifying the antigen-combining sites of anti-DNS antibodies (Reidler et al., *J. Mol. Biol.* (1982) 158:739–746, Oi et al., *Nature* (1984) 307:136–140) and demonstrates that the original DNS combining sites have been re-created in the hybrid antibodies.

Interchain Disulfide Bridges

Each genetically engineered anti-DNS antibody was assembled into H$_2$L$_2$ tetramers as determined using Superose 6 column chromatography. The presence of interchain disulfide bridges was ascertained using non-reducing SDS-PAGE. Eight of ten hybrid immunoglobulins have mobilities characteristic of H$_2$L$_2$ molecules, having both H-L and H-H disulfide bridges. Analysis of the hingeless IgG$_{2a}$ antibody shows H-L molecules and the absence of H$_2$L$_2$ tetramers. This was expected since the cysteines forming the H-H disulfide bridges are located in the hinge region. The two remaining hybrid immunoglobulins have unusual disulfide bridges.

Protein A Binding

The protein A binding of each of the eleven variant antibodies was assessed and used as a probe of Fc structural integrity. Table 1 summarizes the results of this analysis.

TABLE 1

Amino acid residues at positions of protein A contact and protein A binding of hybrid and hinge deleted antibodies.

| Antibody | Contact Residues | | | | | | | | | | | | Protein A Binding |
|---|---|---|---|---|---|---|---|---|---|---|---|---|---|
| | 252 | 253 | 254 | 308 | 309 | 310 | 311 | 312 | 433 | 434 | 435 | 436 | |
| $\gamma_1\gamma_{2a}^{-1}$(IgG2a) | Met | Ile | Ser | Ile | Gln | His | Gln | Asp | His | Asn | His | His | + |
| $\gamma_1\gamma_{2a}^{-2}$ | – | – | – | – | – | – | – | – | – | – | – | – | + |

TABLE 1-continued

Amino acid residues at positions of protein A contact and protein A binding of hybrid and hinge deleted antibodies.

| Antibody | Contact Residues | | | | | | | | | | | | Protein A Binding |
|---|---|---|---|---|---|---|---|---|---|---|---|---|---|
| | 252 | 253 | 254 | 308 | 309 | 310 | 311 | 312 | 433 | 434 | 435 | 436 | |
| $\gamma_1\gamma_{2a}^{-3}$ | – | – | – | – | – | – | – | – | – | – | – | – | + |
| $IgG_{2a}\Delta hinge$ | – | – | – | – | – | – | – | – | – | – | – | – | + |
| $\gamma_1\gamma_{2a}^{-8}(IgG1)$ | Thr | – | Thr | – | Met | – | – | – | – | – | – | – | – |
| $\gamma_1\gamma_{2a}^{-6}$ | Thr | – | Thr | – | Met | – | – | – | – | – | – | – | – |
| $\gamma_1\gamma_{2a}^{-7}$ | Thr | – | Thr | – | Met | – | – | – | – | – | – | – | – |
| $\gamma_1\gamma_1^{-1}$ | Thr | – | Thr | – | Met | – | – | – | – | – | – | – | – |
| $\gamma_1\gamma_1^{-2}$ | Thr | – | Thr | – | Met | – | – | – | – | – | – | – | – |
| $\gamma_1\gamma_{2a}^{-4}$ | Thr | – | Thr | – | – | – | – | – | – | – | – | – | – |
| $\gamma_1\gamma_{2a}^{-5}$ | Thr | – | Thr | – | – | – | – | – | – | – | – | – | – |

Contact residues in $\gamma_1\gamma_{2a}$ are given. EU numbering is used.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for producing a functional immunoglobulin comprising a heavy chain and a light chain, which comprises the steps of:
   (a) transfecting a transformed mammalian lymphocytic cell with a first DNA molecule coding for a first chain of the immunoglobulin;
   (b) transfecting the cell with a second DNA molecule, said second DNA molecule coding for a second chain of the immunoglobulin, said second chain being a chain other than the first chain and said first and second chains being either the heavy chain or the light chain; and
   (c) maintaining the cell in a nutrient medium, so that the cell expresses the first and second DNA molecules and the resultant chains are intracellularly assembled together to form the immunoglobulin which is then secreted in a form capable of specifically binding to antigen
   wherein prior to step (a) the cell does not express a functional immunoglobulin capable of specifically binding antigen.

2. A method as recited in claim 1 wherein the cell is transfected via protoplast fusion.

3. A method as recited in claim 1 wherein the cell is transfected via calcium phosphate precipitation.

4. A method as recited in claim 1 wherein the cell is a myeloma cell.

5. A method as recited in claim 4 wherein the cell is a murine myeloma cell.

6. A method as recited in claim 1 wherein the cell does not endogenously produce any immunoglobulin chains.

7. A method as recited in claim 6 wherein the cell is a murine $P_3$ cell.

8. A method as recited in claim 1 wherein prior to step (a) the cell endogenously produces an immunoglobulin light chain or an immunoglobulin heavy chain, but not both.

9. A method as recited in claim 8 wherein the cell is a murine J558L cell.

10. A method as recited in claim 1 wherein the immunoglobulin comprises the variable region found in a first mammalian species and comprises the constant region found in a second mammalian species, said second mammalian species being other than the first mammalian species.

11. A method for producing a functional immunoglobulin comprising a heavy chain and a light chain, which comprises the steps of:
   (a) transfecting a transformed mammalian lymphocytic cell with a plasmid comprising a first DNA molecule coding for a first chain of the immunoglobulin and a second DNA molecule coding for a second chain of the immunoglobulin, said second chain being a chain other than the first chain and said first and second chains being either the heavy chain or the light chain; and
   (b) maintaining the cell in a nutrient medium so that the cell expresses said first DNA molecule and said second DNA molecule and the resultant chains are intracellularly assembled together to form the immunoglobulin which is then secreted in a form capable of specifically binding to antigen
   wherein prior to step (a) the cell does not express a functional immunoglobulin capable of specifically binding antigen.

12. A method as recited in claim 11 wherein the cell is transfected via protoplast fusion.

13. A method as recited in claim 11 wherein the cell is transfected via calcium phosphate precipitation.

14. A method as recited in claim 11 wherein the cell is a myeloma cell.

15. A method as recited in claim 14 wherein the cell is a murine myeloma cell.

16. A method as recited in claim 11 wherein the cell does not endogenously produce any immunoglobulin chains.

17. A method as recited in claim 16 wherein the cell is a murine $P_3$ cell.

18. A method as recited in claim 11 wherein prior to step (a) the cell endogenously produces an immunoglobulin light chain or an immunoglobulin heavy chain, which endogenously-produced heavy chain is not secreted in a form capable of specifically binding to antigen, but not both.

19. A method as recited in claim 18 wherein the cell is a murine J558L cell.

20. A method as recited in claim 11 wherein the immunoglobulin comprises the variable region found in a first mammalian species and comprises the constant region found in a second mammalian species, said second mammalian species being other than the first mammalian species.

21. A method for producing a functional immunoglobulin comprising a heavy chain and a light chain which comprises the steps of:
  (a) maintaining in a nutrient medium a transformed mammalian lymphocytic cell, said cell having been transfected with a first DNA molecule coding for a first chain of the immunoglobulin and a second DNA molecule coding for a second chain of the immunoglobulin, said second chain being a chain other than the first chain and said first and second chains being either the heavy chain or the light chain;
  (b) expressing from said cell the heavy chain and the light chain functionally assembled together to form said immunoglobulin which is then secreted in a form capable of binding antigen; and
  (c) recovering said immunoglobulin wherein prior to being transfected, the cell does not express a functional immunoglobulin capable of specifically binding antigen.

22. A method as recited in claim 21 wherein the cell is transfected via protoplast fusion.

23. A method as recited in claim 21 wherein the cell is transfected via calcium phosphate precipitation.

24. A method as recited in claim 21 wherein the cell is a myeloma cell.

25. A method as recited in claim 24 wherein the cell is a murine myeloma cell.

26. A method as recited in claim 21 wherein the cell does not endogenously produce any immunoglobulin chains.

27. A method as recited in claim 26 wherein the cell is a murine $P_3$ cell.

28. A method as recited in claim 21 wherein prior to being transfected the cell endogenously produces an immunoglobulin light chain or an immunoglobulin heavy chain, but not both.

29. A method as recited in claim 28 wherein the cell is a murine J558L cell.

30. A method as recited in claim 21 wherein the immunoglobulin comprises the variable region found in a first mammalian source and comprises the constant region found in a second mammalian species, said second mammalian species being other than the first mammalian species.

31. A method for producing a functional antigen-binding protein comprising
  i) a first chain comprising an immunoglobulin heavy chain variable domain and an immunoglobulin heavy chain constant domain and
  ii) a second chain comprising an immunoglobulin light chain variable domain and an immunoglobulin light chain constant domain,
  wherein the method comprises the steps of:
    (a) transfecting a transformed mammalian lymphocytic cell with a first DNA molecule coding for the first chain of the protein;
    (b) transfecting the cell with a second DNA molecule, said second DNA molecule coding for the second chain of the protein; and
    (c) maintaining the cell in a nutrient medium, so that the cell expresses the first and second DNA molecules and the resultant chains are intracellularly assembled together to form the protein which is then secreted in a form capable of specifically binding to antigen
  wherein prior to step (a) the cell does not express a functional antigen-binding protein.

32. A method as recited in claim 31 wherein prior to step (a) the cell does not endogenously produce any immunoglobulin chains.

33. A method as recited in claim 31 wherein prior to step (a) the cell endogenously produces an immunoglobulin light chain or an immunoglobulin heavy chain, but not both.

34. A method as recited in claim 31 wherein the first chain comprises a constant region.

35. A method as recited in claim 31 wherein the heavy and light chain variable domains are from a first mammalian species and the heavy and light chain constant domains are from a second mammalian species, said second mammalian species being other than the first mammalian species.

36. A method as recited in claim 34 wherein the heavy and light chain variable domains are from a first mammalian species and the heavy and light chain constant regions are from a second mammalian species, said second mammalian species being other than the first mammalian species.

37. A method for producing a functional antigen-binding protein comprising
  i) a first chain comprising an immunoglobulin heavy chain variable domain and an immunoglobulin heavy chain constant domain and
  ii) a second chain comprising an immunoglobulin light chain variable domain and an immunoglobulin light chain constant domain,
  wherein the method comprises the steps of:
    (a) transfecting a transformed mammalian lymphocytic cell with a plasmid comprising a first DNA molecule coding for the first chain of the protein and a second DNA molecule coding for the second chain of the protein; and
    (b) maintaining the cell in a nutrient medium so that the cell expresses said first DNA molecule and said second DNA molecule and the resultant chains are intracellularly assembled together to form the protein which is then secreted in a form capable of specifically binding to antigen
  wherein prior to step (a) the cell does not express a functional immunoglobulin capable of specifically binding antigen.

38. A method as recited in claim 37 wherein prior to step (a) the cell does not endogenously produce any immunoglobulin chains.

39. A method as recited in claim 37 wherein prior to step (a) the cell endogenously produces an immunoglobulin light chain or an immunoglobulin heavy chain, but not both.

40. A method as recited in claim 37 wherein the first chain comprises a constant region.

41. A method as recited in claim 39 wherein the antigen-binding protein comprises the heavy and light chain variable domains are from a first mammalian species and comprises the heavy and light chain constant domains are from a second mammalian species, said second mammalian species being other than the first mammalian species.

42. A method as recited in claim 40 wherein the antigen-binding protein comprises the heavy and light chain variable domains are from a first mammalian species and comprises the heavy and light chain constant regions are from a second mammalian species, said second mammalian species being other than the first mammalian species.

43. A method for producing a functional antigen-binding protein comprising
  i) a first chain comprising an immunoglobulin heavy chain variable domain and an immunoglobulin heavy chain constant domain and
  ii) a second chain comprising an immunoglobulin light chain variable domain and an immunoglobulin light chain constant domain, wherein the method comprises the steps of:
(a) maintaining in a nutrient medium a transformed mammalian lymphocytic cell, said cell having been transfected with a first DNA molecule coding for the first chain of the protein and a second DNA molecule coding for the second chain of the protein;
(b) expressing from said cell the first and second chains functionally assembled together to form said protein which is then secreted in a form capable of binding antigen; and
(c) recovering said antigen-binding protein,
wherein prior to being transfected, the cell does not express a functional immunoglobulin capable of specifically binding antigen.

44. A method as recited in claim 43 wherein prior to step (a) the cell does not endogenously produce any immunoglobulin chains.

45. A method as recited in claim 43 wherein prior to step (a) the cell endogenously produces an immunoglobulin light chain or an immunoglobulin heavy chain, but not both.

46. A method as recited in claim 43 wherein the first chain comprises a constant region.

47. A method as recited in claim 43 wherein the heavy and light chain variable domains are from a first mammalian species and the heavy and light chain constant domains are from a second mammalian species, said second mammalian species being other than the first mammalian species.

48. A method as recited in claim 46 wherein the heavy and light chain variable domains are from a first mammalian species and the heavy and light chain constant regions are from a second mammalian species, said second mammalian species being other than the first mammalian species.

49. A transformed mammalian lymphocytic cell producing a functional antigen-binding protein comprising
  i) a first chain comprising an immunoglobulin heavy chain variable domain and an immunoglobulin heavy chain constant domain and
  ii) a second chain comprising an immunoglobulin light chain variable domain and an immunoglobulin light chain constant domain,
  wherein the transformed mammalian lymphocytic cell comprises:
    (a) a first exogenous DNA molecule coding for the first chain of the protein; and
    (b) a second exogenous DNA molecule, said second DNA molecule coding for the second chain of the protein;
wherein without the exogenous DNA molecules the cell does not express a functional antigen-binding protein.

50. A transformed mammalian lymphocytic cell as recited in claim 49 wherein without the exogenous DNA molecules the cell does not endogenously produce any immunoglobulin chains.

51. A transformed mammalian lymphocytic cell as recited in claim 49 wherein without the exogenous DNA molecules the cell endogenously produces an immunoglobulin light chain or an immunoglobulin heavy chain, but not both.

52. A transformed mammalian lymphocytic cell as recited in claim 49 wherein the first chain comprises a constant region.

53. A transformed mammalian lymphocytic cell as recited in claim 49 wherein the heavy and light chain variable domains are from a first mammalian species and the heavy and light chain constant domains are from a second mammalian species, said second mammalian species being other than the first mammalian species.

54. A transformed mammalian lymphocytic cell as recited in claim 52 wherein the heavy and light chain variable domains are from a first mammalian species and the heavy and light chain constant regions are from a second mammalian species, said second mammalian species being other than the first mammalian species.

55. A transformed mammalian lymphocytic cell producing a functional antigen-binding protein comprising
  i) a first chain comprising an immunoglobulin heavy chain variable domain and an immunoglobulin heavy chain constant domain and
  ii) a second chain comprising an immunoglobulin light chain variable domain and an immunoglobulin light chain constant domain,
  wherein the transformed mammalian lymphocytic cell comprises:
    a plasmid comprising a first exogenous DNA molecule coding for the first chain of the protein and a second exogenous DNA molecule coding for the second chain of the protein; and
wherein without the exogenous DNA molecules the cell does not express a functional antigen-binding protein.

56. A transformed mammalian lymphocytic cell as recited in claim 55 wherein without the exogenous DNA molecules the cell does not endogenously produce any immunoglobulin chains.

57. A transformed mammalian lymphocytic cell as recited in claim 55 wherein without the exogenous DNA molecules the cell endogenously produces an immunoglobulin light chain or an immunoglobulin heavy chain, but not both.

58. A transformed mammalian lymphocytic cell as recited in claim 55 wherein the first chain comprises a constant region.

59. A transformed mammalian lymphocytic cell as recited in claim 55 wherein the heavy and light chain variable domains are from a first mammalian species and the heavy and light chain constant domains are from a second mammalian species, said second mammalian species being other than the first mammalian species.

60. A transformed mammalian lymphocytic cell as recited in claim 58 wherein the heavy and light chain variable domains are from a first mammalian species and the heavy and light chain constant regions are from a second mammalian species, said second mammalian species being other than the first mammalian species.

61. A transformed mammalian lymphocytic cell produced by steps (a) and (b) of claim 31.

62. A transformed mammalian lymphocytic cell produced by step (a) of claim 37.

\* \* \* \* \*

UNITED STATES PATENT AND TRADEMARK OFFICE
CERTIFICATE OF CORRECTION

PATENT NO.   : 5,807,715
DATED        : September 15, 1998
INVENTOR(S)  : S.L. Morrison, Herzenberg, L.A. and Oi, V.T.

It is certified that error appears in the above-identified patent and that said Letters Patent is hereby corrected as shown below:

Title page, Item [54], and Column 1, lines 2 and 5,
Delete "LYMPHOCYTE" and replace with -- LYMPHOCYTIC --; after "IMMUNOGLOBULIN", add -- AND FRAGMENTS --.

Item [75], Inventors, delete "Scarsdale, N.Y." and replace with -- Los Angeles --; delete "Menlo Park" and replace with -- Mountain View --; delete "both" and replace with -- all --.

Item [56], in References Cited, after "Seno et al 1983 Nucleic", delete "Acid" and replace with -- Acids --; after "Research 11 (3)", delete ";" and replace with -- : --; and after "Dolby et al 1980 PNAS 77 (10)" add -- : --.

Column 1,
Line 16, add the paragraph -- The work described herein was supported in part by grants from the National Institutes of Health (NIH), including AI-00408, AI-08917, CA-04681, and CA-16858. The United States Government has certain rights in the invention. --
Line 19, delete "1.".
Line 41, delete "2.".
Line 61, after "functional", add -- , --; after "assembled", add -- , --.
Line 66, delete "mouse-" and replace with -- mouse: --.
Line 67, delete ":".

Column 3,
Line 26, delete "prepar" and replace with -- prepara --.
Line 32, delete "CDNA" and replace with -- cDNA --.

Column 4,
Line 45, delete "CDNA" and replace with -- cDNA --.
Line 52, delete "CDNA" and replace with -- cDNA --.
Line 59, delete "CDNA" and replace with -- cDNA --.
Line 65, delete "Joining" and replace with -- joining --.

Column 8,
Line 2, after "immunization", add -- , --.
Line 21, delete "VH" and replace with -- $V_H$ --.
Line 22, delete "Vκ" and replace with -- $V_\kappa$ --.
Line 24, delete "VH" and replace with -- $V_H$ --.
Line 29, delete "Vκ" and replace with -- $V_\kappa$ --.
Line 31, delete "Jκ" and replace with -- $J_\kappa$ --; delete "Cκ" and replace with -- $C_\kappa$ --.

UNITED STATES PATENT AND TRADEMARK OFFICE
CERTIFICATE OF CORRECTION

PATENT NO. : 5,807,715
DATED : September 15, 1998
INVENTOR(S) : S.L. Morrison, Herzenberg, L.A. and Oi, V.T.

It is certified that error appears in the above-identified patent and that said Letters Patent is hereby corrected as shown below:

Column 9,
Line 9, delete "Five" and replace with -- Fine --; delete "Chamicals" and replace with -- Chemicals --.
Line 19, delete "VH-VL" and replace with -- $V_H$-$V_L$ --.
Line 57, delete "H2L2" and replace with -- $H_2L_2$ --.
Line 67, delete "K" and replace with -- $\kappa$ --; delete "antiodies" and replace with -- antibodies --.

Column 10,
Line 5, after "expected" add -- , --.
Line 10, delete "VH" and replace with -- $V_H$ --; delete "Vκ" and replace with -- $V_\kappa$ --.
Line 14, delete "mouse: human" and replace with -- mouse:human --.
Line 22, delete "VH" and replace with -- $V_H$ --; delete "Vκ" and replace with -- $V_\kappa$ --.
Line 36, delete "Mr" and replace with -- $M_r$ --.
Line 42, delete "Mr" and replace with -- $M_r$ --.
Line 54, delete "hybri-doma-" and replace with -- hybridoma --.

Column 11,
Line 5, delete "Vκ" and replace with -- $V_\kappa$ --.
Line 10, delete "mouse: human" and replace with -- mouse:human --.
Line 21, delete "use" and replace with -- used --.
Line 35, delete "$IgG_1$, $IgG_2$, $IgG_3$, $IgG_4$, rabbit IgG and mouse $IgG_3$" and replace with -- IgG1, IgG2, IgG3, IgG4, rabbit IgG and mouse IgG3 --.
Line 37, delete "(delta)" and replace with -- $\Delta$ --.
Line 41, delete "$V_\kappa$" and replace with -- $V_\kappa$ --
Line 43, after "*Ann*" add -- . --.
Line 44, delete "$V_\kappa$" and replace with -- $V_\kappa$ -- .
Line 60, delete "pure, >95%" and replace with -- pure (>95%) --.
Line 63, delete "mouse-human" and replace with -- mouse:human --.
Line 64, delete "$IgG_3$" and replace with -- IgG3 --.

Column 12,
Line 3, delete "$IgG_1$" and replace with -- IgG1 --.
Line 10, delete "affinity purified" and replace with -- affinity-purified --.
Line 22, delete "labelling" and replace with -- labeling --.
Line 26, delete "pp." and replace with -- p. --.
Line 31, after "Kornfeld" add -- , --.
Line 32, delete "Wigzell *Proc*," and replace with -- Wigzell, *Proc.* --.
Line 33, after "et al." add -- , --.
Line 42, delete "$IgG_1$-$IgG_{2a}$" and replace with -- IgG1-IgG2a --.

UNITED STATES PATENT AND TRADEMARK OFFICE
CERTIFICATE OF CORRECTION

PATENT NO. : 5,807,715
DATED : September 15, 1998
INVENTOR(S) : S.L. Morrison, Herzenberg, L.A. and Oi, V.T.

It is certified that error appears in the above-identified patent and that said Letters Patent is hereby corrected as shown below:

Column 12 cont'd,
Line 64, delete "$IgG_1$" and replace with -- IgG1 --; delete "$IgG_2a$" and replace with -- IgG2a --.
Line 65, delete "$IgG_{2a}$" and replace with -- IgG2a --; delete "$IgG_1$" and replace with -- IgG1--.

Column 13,
Line 4, delete "$T_4$" and replace with -- T4 --.
Line 43, after "Gilbert" add -- , --.
Line 65, delete "Dangi" and replace with -- Dangl --

Column 14,
Line 24, delete "bateria" and replace with -- bacteria --.
Line 41, delete "C." and replace with -- C --.
Line 53, delete "labelled" and replace with -- labeled --.

Column 15,
Line 5, delete "$IgG_1$" and replace with -- IgG1 --; delete "$IgG_2a$" and replace with -- IgG2a --.
Line 25, delete "$pHGX1C_{\gamma 2}aB$" and replace with -- $pHGX1C_{\gamma 1}B$ --.
Line 27, delete "$Trp^+$" and replace with -- $TRP^+$ --.
Line 39, delete "$Trp^+$" and replace with -- $TRP^+$ --.
Line 44, delete "$IgG_1$" and replace with -- IgG1 --.
Line 45, delete "$IgG_{2a}$" and replace with -- IgG2a --
Line 46, delete "-7" and replace with -- $^{-7}$ --.
Line 49, delete "$IgG_{2a}$" and replace with -- IgG2a --
Line 50, delete "$IgG_1$" and replace with -- IgG1 --.

Column 16,
Line 2, delete "$IgG_1$" and replace with -- IgG1 --.
Line 3, delete "$IgG_{2a}$" and replace with -- IgG2a --.
Line 18, delete "Mr" and replace with -- $M_r$ --.
Line 29, delete "are" and replace with -- is --; delete "$IgG_1$" and replace with -- IgG1 --.
Line 30, delete "$IgG_{2a}$" and replace with -- IgG2a --.
Line 44, delete "$IgG_{2a}$" and replace with -- IgG2a --.

Column 17,
Line 63, delete "$P_3$" and replace with -- P3 --.

UNITED STATES PATENT AND TRADEMARK OFFICE
CERTIFICATE OF CORRECTION

PATENT NO.    : 5,807,715
DATED         : September 15, 1998
INVENTOR(S)   : S.L. Morrison, Herzenberg, L.A., and Oi, V.T.

It is certified that error appears in the above-identified patent and that said Letters Patent is hereby corrected as shown below:

Column 18,
Line 57, delete "$P_3$" and replace with -- P3 --.

Column 19,
Line 33, delete "$P_3$" and replace with -- P3 --.

Column 20,
Line 50, delete "39" and replace with -- 37 --.
Line 52, delete "are".
Line 53, delete "are".
Line 58, delete "are".
Line 59, delete "are".

Column 21,
Line 13, shift line beginning with "express" to left margin.
Line 14, shift line beginning with "specifically" to left margin.
Line 29, delete "arc" and replace with -- are --.

Column 22,
Line 43, delete "arc" and replace with -- are --.

Signed and Sealed this

Ninth Day of July, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.    : 5,807,715
DATED         : September 15, 1998
INVENTOR(S)   : S.L. Morrison, Herzenberg, L.A. and Oi, V.T.

It is certified that error appears in the above-identified patent and that said Letters Patent is hereby corrected as shown below:

<u>Title page, Item [54] and Column 1, Lines 1 and 5,</u>
Item [54], delete "LYMPHOCYTE" and replace with -- LYMPHOCYTIC --; after "IMMUNOGLOBULIN", add -- AND FRAGMENTS --.
Item [75], Inventors, delete "Scarsdale, N.Y." and replace with -- Los Angeles --; delete "Menlo Park" and replace with -- Mountain View --; delete "both" and replace with -- all --.
Item [73], Assignee, delete "Assignee" and replace with -- Assignees --; after "Calif." add -- , and The Trustees of Columbia University, New York, N.Y. --.
Item [56], References Cited, after "Seno, et al 1983 Nucleic", delete "Acid" and replace with -- Acids --; after "Research 11 (3)", delete ";" and replace with -- . --; and after "Dolby et al 1980 PNAS 77 (10)" add -- : --.

<u>Column 1,</u>
Line 16, add the paragraph -- The work described herein was supported in part by grants from the National Institutes of Health (NIH), including AI-00408, AI-08917, CA-04681, and CA-16858. The United States Government has certain rights in the invention. --
Line 19, delete "1.".
Line 41, delete "2.".
Line 61, after "functional", add -- , --; after "assembled", add -- , --.
Line 66, delete "mouse-" and replace with -- mouse: --
Line 67, delete ":".

<u>Column 3,</u>
Line 26, delete "prepar" and replace with -- prepara --.
Line 32, delete "CDNA" and replace with -- cDNA --.

<u>Column 4,</u>
Line 45, delete "CDNA" and replace with -- cDNA --.
Line 52, delete "CDNA" and replace with -- cDNA --.
Line 59, delete "CDNA" and replace with -- cDNA --.
Line 65, delete "Joining" and replace with -- joining --..

UNITED STATES PATENT AND TRADEMARK OFFICE
CERTIFICATE OF CORRECTION

PATENT NO.   : 5,807,715
DATED        : September 15, 1998
INVENTOR(S)  : S.L. Morrison, Herzenberg, L.A. and Oi, V.T.

It is certified that error appears in the above-identified patent and that said Letters Patent is hereby corrected as shown below:

Column 8,
Line 2, after "immunization", add -- , --.
Line 21, delete "VH" and replace with -- $V_H$ --.
Line 22, delete "Vκ" and replace with -- $V_\kappa$ -- (Greek letter kappa subscripted).
Line 24, delete "VH" and replace with -- $V_H$ --.
Line 29, delete "Vκ" and replace with -- $V_\kappa$ -- (Greek letter kappa subscripted).
Line 31, delete "Jκ" and replace with -- $J_\kappa$ -- (Greek letter kappa subscripted); delete "Cκ" and replace with -- $C_\kappa$ --. (Greek letter kappa subscripted).

Column 9,
Line 9, delete "Five" and replace with -- Fine --; delete "Chamicals" and replace with -- Chemicals --.
Line 19, delete "VH-VL" and replace with -- $V_H$-$V_L$ --.
Line 57, delete "H2L2" and replace with -- $H_2L_2$ --.
Line 67, delete "K" and replace with -- $\kappa$ --; delete "antiodies" and replace with -- antibodies --.

Column 10,
Line 5, after "expected" add -- , --.
Line 10, delete "VH" and replace with -- $V_H$ --; delete "VK" and replace with -- $V_\kappa$ -- (Greek letter kappa subscripted).
Line 14, delete "mouse: human" and replace with -- mouse:human --.
Line 22, delete "VH" and replace with -- $V_H$ --; delete "Vκ" and replace with -- $V_\kappa$ -- (Greek letter kappa subscripted).
Line 36, delete "Mr" and replace with -- $M_r$ --.
Line 42, delete "Mr" and replace with -- $M_r$ --.
Line 54, delete "hybri-doma-" and replace with -- hybridoma --.

UNITED STATES PATENT AND TRADEMARK OFFICE
CERTIFICATE OF CORRECTION

PATENT NO.    : 5,807,715
DATED         : September 15, 1998
INVENTOR(S)   : S.L. Morrison, Herzenberg, L.A. and Oi, V.T.

It is certified that error appears in the above-identified patent and that said Letters Patent is hereby corrected as shown below:

Column 11,
Line 5, delete "Vκ" and replace with -- $V_\kappa$ -- (Greek letter kappa subscripted).
Line 10, delete "mouse: human" and replace with -- mouse:human --.
Line 21, delete "use" and replace with -- used --.
Line 35, delete "$IgG_1$, $IgG_2$, $IgG_3$, $IgG_4$, rabbit IgG and mouse $IgG_3$" and replace with -- IgG1, IgG2, IgG3; IgG4, rabbit IgG and mouse IgG3 --.
Line 37, delete "(delta)" and replace with -- $\Delta$ -- (Greek letter capital delta).
Line 41, delete "VK" and replace with -- $V_\kappa$ -- (Greek letter kappa subscripted).
Line 43, after "Ann" add -- . --.
Line 44, delete "Vκ" and replace with -- $V_\kappa$ -- (Greek letter kappa subscripted).
Line 60, delete "pure, >95%" and replace with -- pure (>95%) --.
Line 63, delete "mouse-human" and replace with -- mouse:human --.
Line 64, delete "$IgG_3$" and replace with -- IgG3 --.

Column 12,
Line 3, delete "$IgG_1$" and replace with -- IgG1 --.
Line 10, delete "affinity purified" and replace with -- affinity-purified --.
Line 22, delete "labelling" and replace with -- labeling --.
Line 26, delete "pp." and replace with -- p. --.
Line 31, after "Kornfeld" add -- , --.
Line 32, delete "Wigzell *Proc*," and replace with -- Wigzell, *Proc.* --.
Line 33, after "et al." add -- , --.
Line 42, delete "$IgG_1$-$IgG_{2a}$" and replace with -- IgGl-IgG2a --.
Line 64, delete "$IgG_1$" and replace with -- IgG1 --; delete "$IgG_2$a" and replace with -- IgG2a --.
Line 65, delete "$IgG_{2a}$" and replace with -- IgG2a --; delete "$IgG_1$" and replace with -- IgG1 --.

Column 13,
Line 4, delete "$T_4$" and replace with -- T4 --.
Line 43, after "Gilbert" add -- , --.
Line 65, delete "Dangi" and replace with -- Dangl --.

Column 14,
Line 24, delete "bateria" and replace with -- bacteria --.
Line 41, delete "C." and replace with -- C --.
Line 53, delete "labelled" and replace with -- labeled --.

UNITED STATES PATENT AND TRADEMARK OFFICE
CERTIFICATE OF CORRECTION

PATENT NO. : 5,807,715
DATED : September 15, 1998
INVENTOR(S) : S.L. Morrison, Herzenberg, L.A. and Oi, V.T.

It is certified that error appears in the above-identified patent and that said Letters Patent is hereby corrected as shown below:

Column 15,
Line 5, delete "$IgG_1$" and replace with -- IgG1 --; delete "$IgG_2a$" and replace with -- IgG2a --.
Line 25, delete "$pHGXIC_{Y2}aB$" and replace with -- $pHGXlC_{Y1}B$ -- .
Line 27, delete "Trp·" and replace with -- $TRP^+$ --.
Line 39, delete "Trp·" and replace with -- $TRP^+$ --.
Line 44, delete "$IgG_1$" and replace with -- IgG1 --.
Line 45, delete "$IgG_{2a}$" and replace with -- IgG2a --.
Line 49, delete "$IgG_{2a}$" and replace with -- IgG2a --.
Line 50, delete "$IgG_1$" and replace with -- IgG1 --.
Line 46, delete "-7" and replace with -- $^{-7}$ --.

Column 16,
Line 2, delete "$IgG_1$" and replace with -- IgG1 --.
Line 3, delete "$IgG_{2a}$" and replace with -- IgG2a --.
Line 18, delete "Mr" and replace with -- $M_r$ --.
Line 29, delete "are" and replace with -- is --; delete "$IgG_1$" and replace with -- IgG1 --.
Line 30, delete "$IgG_{2a}$" and replace with -- IgG2a --.
Line 44, delete "$IgG_{2a}$" and replace with -- IgG2a --.

Column 17,
Line 63, delete "$P_3$" and replace with -- P3 --.

Column 18,
Line 57, delete "$P_3$" and replace with -- P3 --.

Column 19,
Line 33, delete "$P_3$" and replace with -- P3 --.

Column 20,
Line 50, delete "39" and replace with -- 37 --.
Line 52, delete "are".
Line 53, delete "are".
Line 58, delete "are".
Line 59, delete "are"

UNITED STATES PATENT AND TRADEMARK OFFICE
CERTIFICATE OF CORRECTION

PATENT NO.   : 5,807,715
DATED        : September 15, 1998
INVENTOR(S)  : S.L. Morrison, Herzenberg, L.A. and Oi, V.T.

It is certified that error appears in the above-identified patent and that said Letters Patent is hereby corrected as shown below:

Column 21,
Line 13, shift line beginning with "express" to left margin.
Line 14, shift line beginning with "specifically" to left margin.
Line 29, delete "arc" and replace with -- are --.

Column 22,
Line 43, delete "arc" and replace with -- are --.

This certificate supersedes the Certificate of Correction issued July 9, 2002.

Signed and Sealed this

Sixth Day of August, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.     : 5,807,715                                        Page 1 of 1
DATED          : September 15, 1998
INVENTOR(S)    : Sherie L. Morrison et al.

It is certified that error appears in the above-identified patent and that said Letters Patent is hereby corrected as shown below:

Title page,
Item [73], Assignee, should read as follows:
-- The Board of Trustees of The Leland Stanford Junior University, Stanford, CA; and The Trustees of Columbia University in the City of New York, New York, NY --.

Signed and Sealed this

Eighteenth Day of May, 2004

JON W. DUDAS
*Acting Director of the United States Patent and Trademark Office*